(12) United States Patent
Cavallaro

(10) Patent No.: US 9,669,099 B2
(45) Date of Patent: Jun. 6, 2017

(54) PINE BARK EXTRACT AND BLACK PEPPER ESSENTIAL OIL WITH ANTI-INFLAMMATORY AND ANTI-ARTHRITIC ACTION AND METHOD OF PREPARING SAME

(71) Applicant: Antonino Cavallaro, Miami, FL (US)

(72) Inventor: Antonino Cavallaro, Miami, FL (US)

( * ) Notice: Subject to any disclaimer, the term of this patent is extended or adjusted under 35 U.S.C. 154(b) by 228 days.

(21) Appl. No.: 14/731,097

(22) Filed: Jun. 4, 2015

(65) Prior Publication Data

US 2016/0354471 A1    Dec. 8, 2016

(51) Int. Cl.
| | | |
|---|---|---|
| *A61K 36/00* | (2006.01) |
| *A61K 47/32* | (2006.01) |
| *A61K 9/00* | (2006.01) |
| *A61K 31/355* | (2006.01) |
| *A61K 9/06* | (2006.01) |
| *A61K 36/67* | (2006.01) |
| *A61K 36/15* | (2006.01) |
| *A61K 47/10* | (2017.01) |

(52) U.S. Cl.
CPC ............ *A61K 47/32* (2013.01); *A61K 9/0014* (2013.01); *A61K 9/06* (2013.01); *A61K 31/355* (2013.01); *A61K 36/15* (2013.01); *A61K 36/67* (2013.01); *A61K 47/10* (2013.01); *A61K 2300/00* (2013.01)

(58) Field of Classification Search
None
See application file for complete search history.

*Primary Examiner* — Qiuwen Mi
(74) *Attorney, Agent, or Firm* — Mark Terry

(57) ABSTRACT

A gel for topical application, comprising of: about 37.0 percent by weight of deionized water; about 0.3 percent by weight of acrylate crosspolymer; about 0.05 percent by weight of glycerin; about 0.2 percent by weight of tocopherol acetate; about 0.15 percent by weight of pine bark extract; about 2.0 percent by weight of black pepper essential oil; about 60.0 percent by weight of isopropyl alcohol SDA; about 0.1 percent by weight of ethylenediamine tetraacetic acid; and, about 2.0 percent by weight of a preservative mixture solution comprising 3 percent by weight of propylparaben, 11 percent by weight of methylparaben and 30 percent by weight of diazolinyl urea.

3 Claims, 14 Drawing Sheets

200
PRIOR ART
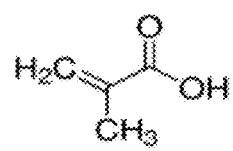
Metacrylic acid
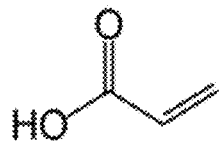
Acrylic acid
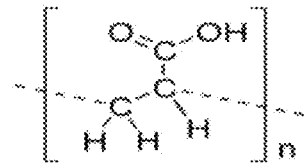
Polyacrylic acid
FIG. 2

300

PRIOR ART

400

PRIOR ART

700

PRIOR ART

Table 1. Retention time and mass spectral data of the compounds characterized in pine bark extract by HPLC-ESI-QTOF-MS and MS/MS in negative mode.

| Peak | Proposed Compound | RT (min) | [M-H]⁻ Measured | [M-H]⁻ Calculated | Error (ppm) | mSigma | Fragmentation Pattern | Molecular Formula | Ref. |
|---|---|---|---|---|---|---|---|---|---|
| 1 | Sucrose | 5.4 | 3,411,098 | 3,411,089 | 2.6 | 9 | non fragmented | C₁₂H₂₂O₁₁ | -- |
| 2 | Procyanidin C | 11.3 | 8,651,981 | 8,651,985 | 0.5 | 30 | 577, 289 | C₄₅H₃₈O₁₈ | [1,13,15,24-27] |
| 3 | Gardenoside | 12.4 | 4,031,257 | 4,031,246 | 2.7 | 6.2 | non fragmented | C₁₇H₂₄O₁₁ | -- |
| 4 | Procyanidin A (isomer 1) | 13.3 | 5,751,191 | 5,751,195 | 0.6 | 22 | 289 | C₃₀H₂₄O₁₂ | -- |
| 5 | Procyanidin A (isomer 2) | 13.9 | 5,751,189 | 5,751,195 | 1 | 34.8 | 289 | C₃₀H₂₄O₁₂ | -- |
| 6 | Procyanidin B (isomer 1) | 14.7 | 5,771,366 | 5,771,351 | 2.6 | 5.3 | 425 | C₃₀H₂₆O₁₂ | [1,13,15,24-27] |
| 7 | Procyanidin B (isomer 2) | 15.9 | 5,771,347 | 5,771,351 | 0.7 | 13.2 | 425, 289 | C₃₀H₂₆O₁₂ | [1,13,15,24-27] |
| 8 | Chalcan-flavan-3-ol dimer (isomer 1) | 16.7 | 5,791,532 | 5,791,508 | 4.2 | 5.2 | 561 | C₃₀H₂₈O₁₂ | -- |
| 9 | Procyanidin trimer A-type (isomer 1) | 17 | 8,631,842 | 8,631,829 | 0.4 | 27.4 | 289, 285 | C₄₅H₃₆O₁₈ | -- |
| 10 | (-)-epicatechin | 17.9 | 2,890,727 | 2,890,718 | 3.4 | 4.9 | 245 | C₁₅H₁₄O₆ | [1,13,15,24-27] |
| 11 | Chalcan-flavan-3-ol dimer (isomer 2) | 18.3 | 5,791,512 | 5,791,508 | 0.7 | 4.3 | 289 | C₃₀H₂₈O₁₂ | -- |
| 12 | Chalcan-flavan-3-ol dimer (isomer 3) | 18.8 | 579,152 | 5,791,508 | 2.1 | 6.2 | 561, 289 | C₃₀H₂₈O₁₂ | -- |
| 13 | Chalcan-flavan-3-ol dimer (isomer 4) | 19.1 | 5,791,528 | 5,791,508 | 3.5 | 6.5 | 561 | C₃₀H₂₈O₁₂ | -- |
| 14 | Procyanidin trimer A-type (isomer 2) | 19.4 | 8,631,869 | 8,631,829 | 4.6 | 10.3 | 289 | C₄₅H₃₆O₁₈ | -- |
| 15 | Chalcan-flavan-3-ol dimer (isomer 5) | 19.8 | 5,791,516 | 5,791,508 | 1.3 | 5 | 561, 289 | C₃₀H₂₈O₁₂ | -- |
| 16 | Chalcan-flavan-3-ol dimer (isomer 6) | 20.4 | 579,152 | 5,791,508 | 2 | 4 | 561 | C₃₀H₂₈O₁₂ | -- |
| 17 | (Epi)fisetinidol-(epi)catechin (isomer 1) | 20.8 | 5,611,422 | 5,611,402 | 3.4 | 5.9 | 273 | C₃₀H₂₆O₁₁ | -- |
| 18 | Procyanidin A (isomer 3) | 21.2 | 5,751,195 | 5,751,195 | 0.1 | 18.9 | 289 | C₃₀H₂₄O₁₂ | -- |
| 19 | (Epi)fisetinidol-(epi)catechin (isomer 2) | 21.7 | 5,611,428 | 5,611,402 | 4.7 | 6.3 | 289, 273 | C₃₀H₂₆O₁₁ | -- |
| 20 | (+)-catechin | 22.7 | 2,890,729 | 2,890,718 | 3.8 | 7.8 | 245 | C₁₅H₁₄O₆ | [1,13,15,24-27] |
| 21 | (Epi)fisetinidol-(epi)catechin (isomer 3) | 23.8 | 5,611,406 | 5,611,402 | 0.6 | 38.5 | 289 | C₃₀H₂₆O₁₁ | -- |
| 22 | (Epi)fisetinidol-(epi)catechin (isomer 4) | 24.4 | 5,611,409 | 5,611,402 | 1.1 | 9.6 | 273 | C₃₀H₂₆O₁₁ | -- |
| 23 | Procyanidin A (isomer 4) | 25 | 5,751,203 | 5,751,195 | 2 | 8 | 423 | C₃₀H₂₄O₁₂ | -- |
| 24 | (Epi)fisetinidol-(epi)catechin (isomer 5) | 25.9 | 5,611,413 | 5,611,402 | 2 | 2.7 | non fragmented | C₃₀H₂₆O₁₁ | -- |
| 25 | Procyanidin A (isomer 5) | 26.3 | 5,751,188 | 5,751,195 | 1.3 | 12.7 | 289 | C₃₀H₂₄O₁₂ | -- |

PRIOR ART

FIG. 9

PRIOR ART

Table 1. Cont.

| Peak | Proposed Compound | RT (min) | [M-H]⁻ Measured | [M-H]⁻ Calculated | Error (ppm) | mSigma | Fragmentation Pattern | Molecular Formula | Ref. |
|---|---|---|---|---|---|---|---|---|---|
| 26 | Procyanidin A (isomer 6) | 27.5 | 5,751,221 | 5,751,195 | 4.6 | 21.8 | 289 | C₃₀H₂₄O₁₂ | — |
| 27 | (Epi)fisetinidol-(epi)catechin (isomer 6) | 28.3 | 5,611,492 | 5,611,402 | 0 | 5 | non fragmented | C₃₀H₂₆O₁₁ | — |
| 28 | (Epi)fisetinidol-(epi)catechin (isomer 7) | 29.8 | 5,611,416 | 5,611,402 | 2.3 | 3 | 289, 273 | C₃₀H₂₆O₁₁ | — |
| 29 | Procyanidin A (isomer 7) | 30.7 | 57,512 | 5,751,195 | 0.8 | 14.3 | 289 | C₃₀H₂₄O₁₂ | — |
| 30 | (Epi)fisetinidol-(epi)catechin (isomer 8) | 31.1 | 56,114 | 5,611,402 | 0.5 | 11.8 | 245 | C₃₀H₂₆O₁₁ | — |
| 31 | Procyanidin A (isomer 8) | 32.7 | 5,751,205 | 5,751,195 | 1.7 | 10.7 | 285 | C₃₀H₂₄O₁₂ | — |
| 32 | (Epi)fisetinidol-(epi)catechin (isomer 9) | 33.4 | 5,611,418 | 5,611,402 | 2.8 | 7.9 | 289 | C₃₀H₂₆O₁₁ | — |
| 33 | Quercetin rhamnosylrutinoside | 34.2 | 7,552,041 | 755,204 | 0.2 | 11.9 | 301 | C₃₃H₄₀O₂₀ | [28] |
| 34 | Rutin | 36.3 | 6,091,476 | 6,091,461 | 0.7 | 14.4 | 301 | C₂₇H₃₀O₁₆ | [28] |
| 35 | Isorhamnetin rutinoside | 41.1 | 6,231,614 | 6,231,618 | 0.6 | 10.5 | 315 | C₂₈H₃₂O₁₆ | [25] |
| 36 | Quercetin | 45.8 | 3,010,357 | 3,010,354 | 0.9 | 7.4 | non fragmented | C₁₅H₁₀O₇ | [28,29] |
| 37 | Kaempferol | 49 | 285,041 | 2,850,405 | 1.7 | 11.2 | non fragmented | C₁₅H₁₀O₆ | [30,31] |

FIG. 10

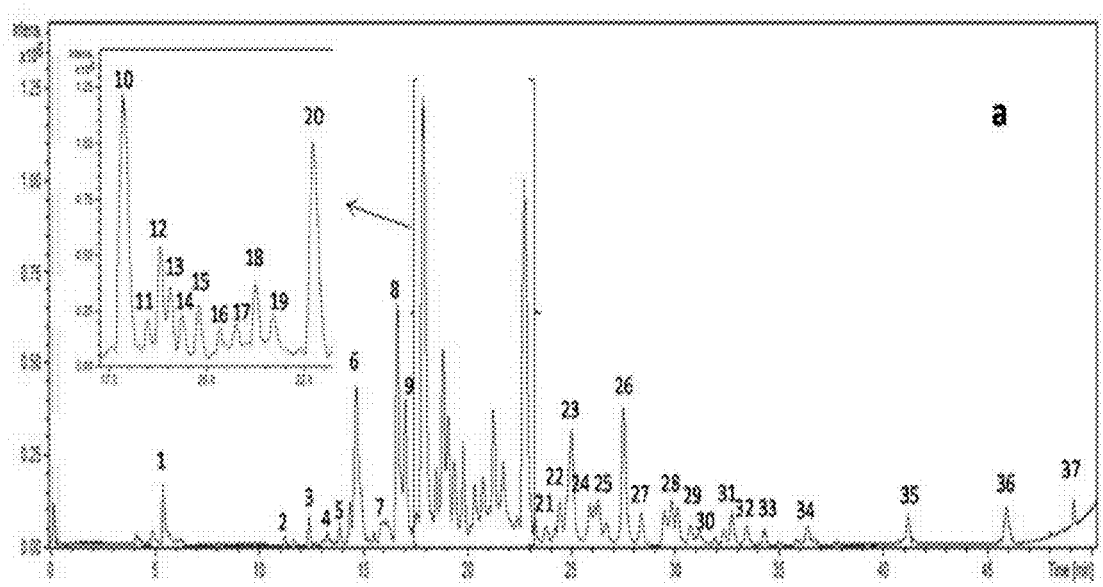
PRIOR ART	FIG. 11

| Physical property | Value |
|---|---|
| Viscosity (mPa.s) | 6,000-14,000 |
| pH | 4.0 – 5.0 |
| Yield value (dyn/cm2) (initial resistance to flow under stress, yield stress) | 1000-2000 |
| Turbidity (NTU, Nephelometric Turbidity Units) | < 20 |
| Stability | Passed 3 months to 45 C , 5 cycles freeze/thaw |

FIG. 14

PINE BARK EXTRACT AND BLACK PEPPER ESSENTIAL OIL WITH ANTI-INFLAMMATORY AND ANTI-ARTHRITIC ACTION AND METHOD OF PREPARING SAME

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The present invention relates to generally to anti-inflammatory compositions, and more specifically, to anti-inflammatory and analgesic compositions derived from pine bark extract and black pepper essential oil to alleviate pain and inflammation at site.

BACKGROUND

Anti-inflammatory painkillers are a genre of medicine that can be utilized to alleviate pains, sprains, strains and other common effects of arthritis. They can be consumed orally in the form of tablets, liquids or capsules, injected via needle, or applied to skin in the form of a topical gel or cream. The mechanisms of action of either of these when used as anti-inflammatories is varied.

When applied to skin in the form of a topical preparation, the anti-inflammatory painkillers are sometimes called topical non-steroidal anti-inflammatory drugs (NSAIDs) or just topical anti-inflammatories as a generic term. The NSAIDs are often prescribed as a preliminary treatment for mild to moderate musculoskeletal pain, sprains, strains, and arthritis. High plasma concentrations of oral NSAIDs are required to achieve effective tissue concentrations at the site of pain and inflammation.

In an attempt to find relief of musculoskeletal pain with NSAIDs, topical application NSAID's have been developed to deliver adequate local tissue concentrations with minimal systematic absorption. It has been found that plasma concentrations following topical administration of NSAIDs gels are far lower than levels found after oral administration.

NSAIDs work in the same way as oral anti-inflammatory painkillers, in which the oral anti-inflammatories when taken my mouth, work to inhibit or block the effect of chemicals called cyclo-oxygenase (COX) enzymes. COX enzymes typically aid in the production of prostaglandins, some of which assist in the production of pain and inflammation at site. A reduction in prostaglandin production means lesser pain and inflammation. NSAIDs specifically work only on the area that the topical gel has been applied to rather than the entire body like their oral painkiller counterparts. When topically applied, the NSAIDs are absorbed into the skin of the user and move deeper into the areas of the body like the muscle itself, where there is pain and inflammation exists at site. Using NSAIDs in the form of topical preparation can mean that the total amount of anti-inflammatory in the user's body is very low. This could also mean that that the user is less likely to encounter any potential side-effects due to such use.

NSAIDs used regularly for sports injuries, painful joints and arthritis are effective to treat inflammation, however they present skin side effects that can become severe in some people. The topical diclofenac gel has presented allergic contact dermatitis, dryness (irritant dermatitis) and scaling. Also the use of topical NSAID gels or creams to treat pain has been reported to cause a photocontact dermatitis. It has been observed that the reaction appears after stopping the application where the skin is exposed to sunlight. It has also been observed that NSAID gels can produce exanthema, itch, morbilliform, rash, photosensitivity, urticaria and angioedema.

On the other hand, while topical steroids have important benefit in reducing inflammation, they also have significant side effects. Most of the side-effects are seen in long-term use, but some may also be seen within days of starting such a therapy. Side effects consist of: 1) skin atrophy, which causes the thinning of the epidermis and changes in the connective tissue of the dermis, wrinkled skin, hypopigmentation and prominence of underlying veins, 2) alteration in immune function, which can inhibit the skin's ability to fight off bacterial or fungal infections, 3) tachyphylaxis, the tolerance the skin develops to the vaso-constrictive action of topical steroids, 4) steroid rosacea, which is redness and pustules as commonly observed in fair skinned people, 5) topical steroid allergy, which has been observed in 4 to 5 percent of people who use topical steroids, 6) stretch marks in areas where the skin touches skin such as groin and armpits, most of which are itchy, permanent and irreversible, 7) immune-suppression, which is caused when topical steroids are used to skin infection of fungal origin causing the user to get a rash that gets redder, itchier and spreads more extensively than a typical fungal infection. As a result, there is a widespread pustular inflammation called tinea incognito.

Therefore, a need exists to overcome the problems with the prior art as discussed above, and particularly for a more efficient way of providing an anti-inflammatory and analgesic composition.

SUMMARY

This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

The disclosed embodiments are directed to a formulation, where the anti-inflammatory and analgesic activities of black pepper essential oil and pine bark extract within a precise proportion of gel matrix to obtain an effective analgesic and anti-inflammatory topical preparation. The topical gel may relieve inflammatory conditions of various origins and pain associated with inflammatory conditions of various origins at the localized area.

The gel for topical application is disclosed, comprising of: about 37.0 percent by weight of deionized water; about 0.3 percent by weight of acrylate crosspolymer; about 0.05 percent by weight of glycerin; about 0.2 percent by weight of tocopherol acetate; about 0.15 percent by weight of pine bark extract; about 2.0 percent by weight of black pepper essential oil; about 60.0 percent by weight of isopropyl alcohol SDA; about 0.1 percent by weight of ethylenediamine tetraacetic acid; and, about 2.0 percent by weight of a preservative mixture solution comprising 3 percent by weight of propylparaben and 11 percent by weight of methylparaben and 30 percent by weight of diazolinyl urea.

In another embodiment, a method of preparation of gel is disclosed. The method includes the steps of: sprinkling acrylate crosspolymer on a surface of deionized water; mixing the acrylate crosspolymer and the deionized water; dissolving isopropyl alcohol SDA in the acrylate crosspolymer and deionized water and mixing; adding in the following ingredients one at a time: glycerin, tocopherol acetate, pine bark extract, black pepper essential oil, a preservative mixture solution comprising propylparaben, methylparaben and diazolinyl urea and mixing.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims. The foregoing and other features and advantages of the present invention will be apparent from the following more particular description of the preferred embodiments of the invention, as illustrated in the accompanying drawings.

BRIEF DESCRIPTION OF THE DRAWINGS

The accompanying drawings, which are incorporated in and constitute part of this specification, illustrate embodiments of the invention and together with the description, serve to explain the principles of the disclosed embodiments. The embodiments illustrated herein are presently preferred, it being understood, however, that the invention is not limited to the precise arrangements and instrumentalities shown, wherein:

FIG. 2 is a perspective view of the molecular structure of acrylate crosspolymers;

FIGS. 9 and 10 is a table listing a characterization of constituents from pine bark extract;

FIG. 11 is a peak chromatogram illustrating a characterization of constituents from pine bark extract.

DETAILED DESCRIPTION

Figure 1:
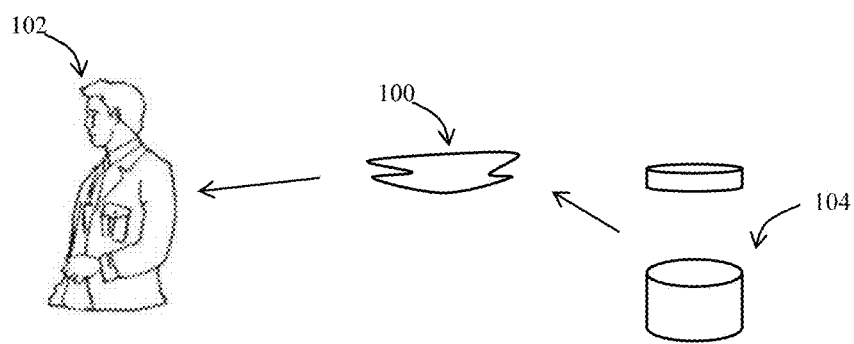
FIG. 1 is a view of an embodiment of the pine bark extract and black pepper essential oil depicting its use.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering, or adding additional stages or components to the disclosed methods and devices. Accordingly, the following detailed description does not limit the disclosed embodiments. Instead, the proper scope of the disclosed embodiments is defined by the appended claims.

The disclosed embodiments include pine bark extract and black pepper essential oil, excipients, natural enhancers, and alcohol that exert their action via a temporary alteration of barrier properties of the skin, to enhance the delivery of the active ingredients. The preparation, in addition to its main anti-inflammatory and anti-arthritic property, has a rapid effect, can be used wearing any clothes that will not spoil or stain on contact, lacks any fragrance making it undetectable, and it is simple to apply. The vehicle itself has a cooling emollient and protective action in the formulation. The preservatives added protect the formulation from microbial and mold growth as well as from the occurrence of rancidity in its oil base.

The disclosed embodiments include a formulation, where the anti-inflammatory and analgesic activities of pine bark extract and black pepper essential oils are enhanced within an appropriate gel matrix to obtain an effective analgesic and anti-inflammatory topical preparation that can be effectively and easily applied to the site of pain. Musculoskeletal pains can be alleviated by the use of suitable topical formulation pine bark extract and black pepper essential oil delivery system. The disclosed embodiments for topical application with anti-inflammatory and anti-arthritic action contains pine bark extract and black pepper essential oil as active agents. The combination of both active ingredients complement and synergize yielding anti-inflammatory and anti-arthritic effects upon use.

The disclosed embodiments may ease inflammation, muscle pains, strains, and sprains. It can also ease the pain associated with arthritis, iliotibial band syndrome, plantar fasciitis, shin splints, common tendinitis such as lateral epicondylitis, achilles tendinitis, patellar tendinitis, and carpal tunnel syndrome and bursitis. The disclosed embodiments can be applied at the localized site, thus preventing the harshness of orally consumed NSAIDs, which may have adverse effects on gastrointestinal tracts of the user due to active ingredients such as ibuprofen, diclofenac, felbinac, ketoprofen, or piroxicam that may cause digestive issues.

FIG. 1 is a view of the disclosed embodiments depicting its use. FIG. 1 shows that the composition 100 may be stored and distributed in a container 104. Subsequently, the composition 100 may be removed from the container 104 and applied to the afflicted site on the patient 102. The composition 100 is structured to be applied topically to the skin in small amounts to cure the patient's affliction, such as inflammation of the skin. A small amount is defined as an amount of gel that easily fits on the finger or hand of the applying individual. A regimen may be used with the composition 100, such as applying the composition 100 to the patient's skin periodically, such as once a day, every morning, for a defined period of time, such as for two weeks.

As used herein the following terms are intended to have meaning as follows: namely, "anti-inflammatory composition" "composition" and "formulation" meaning pharmaceutical compositions formulated and compounded with a topical gel matrix.

"Gel" or "gel matrix" meaning a colloid that is basically 99% by weight of liquid which is immobilized by surface tension between it and macromolecular network of fibers built from a small amount of a substance gelating material present. Gel or gel matrix may include Carbopol® Aqua CC polymer/acrylate crosspolymer, and the like. As used herein, "acrylate crosspolymer" may be intended to mean "Carbopol® Aqua CC polymer".

Acrylate crosspolymers are rheology modifiers, crosslinked polyacrylic acid for thickening, suspending, and as a stabilizer agent used in a wide variety of personal care products. It delivers excellent thickening efficiency and suspending capability, long viscous flow and sparkling clarity in gel systems. It is characterized by dispersing and "swelling" in aqueous media, forming gels and sols displaying fairly high viscosity. These qualities integrate more stable and clear as well as gelling properties, perfectly contrasted against pH. Crosslinked alkyl acrylates are reported to function as absorbents, film formers, emulsion stabilizers, viscosity increasing agents, suspending agents, binders, and/or skin conditioning agents in cosmetic formulations. Acrylate copolymer is a general term for copolymers of two or more monomers consisting of acrylic acid, methacrylic acid or one of their simple esters as represented by the structures 200 shown in FIG. 2. The gel of the disclosed embodiments comprises about 0.3 percent by weight of acrylate crosspolymer. In an embodiment where 100 grams of said gel are produced, the gel of the disclosed embodiments comprises about 0.3 grams of acrylate crosspolymer.

In addition, Carbopol® Aqua CC polymer may also comprise: amino substituents, which provide hydrophilicity and cationic properties at low pH; hydrophobic substituents which moderate the hydrophilicity; hydrophobic ally modified polyoxyalkylene substituents which provide associative properties; crosslinker—the unique design of this polymer features an optimized balance of hydrophilic and hydrophobic character, with amine functionality which further activates ionic (cationic) characteristics at low pH (in use). Importantly, the polymer incorporates a proprietary modified hydrophobe package which enables controlled associative thickening and provides enhanced rheological properties.

Figure 3:
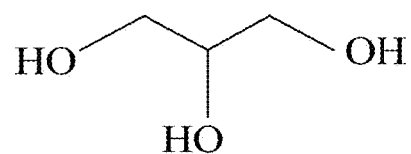
FIG. 3 is a perspective view of the molecular structure of glycerin.

"Glycerin" meaning "Gliceryn," "Glycerol," "Glycerine," "1,2,3-Propanetriol," "Glyceritol," "Glycyl alcohol," "Trihydroxypropane," "Propanetriol," "Osmoglyn," and "1,2,3-trihydroxypropane" is a trihydroxy sugar alcohol with three hydroxyl groups that are responsible for its solubility in water and its hygroscopic nature and may function in the composition as humectant, improving smoothness, providing lubrication, emollient agent, skin conditioning agent, skin protector, and viscosity decreasing agent as represented by the structure 300 shown in FIG. 3.

Glycerin is widely used as humectantin cosmetics and personal care products, also as hair conditioning agent, in skin creams and lotions, in shaving preparations, deodorants, make up, oral care agent, skin conditioning agent, and viscosity decreasing agents. Glycerine is virtually nontoxic, non-irritating, and odorless. It functions as a humectant, vehicle, and emollient. The U.S. Food and Drug Administration (FDA) includes glycerin on its list of direct food additives considered Generally Recognized As Safe (GRAS), and on its list of approved indirect food additives. Glycerin is also an FDA approved active ingredient in Over-the-Counter (OTC) skin protectant drug products, ear drying products and it an approved demulcent for the eyes. Glycerin in the formulation is required such as humectants and emollient agent, skin conditioning agent, skin protector, and viscosity decreasing agents. The gel for the present formulation comprises about 0.05 percent by weight of glycerin. In an embodiment where 100 grams of said gel are produced, the gel of the disclosed embodiments comprises about 0.5 grams of glycerin.

"Deionized water" meaning "demineralized water"/"DM water", "DI water", "DIW" or "de-ionized water"), is water that has had almost all of its mineral ions removed, such as cations like sodium, calcium, iron, and copper, and anions such as chloride and sulfate. "Deionized water" meaning water that is treated with a chelating agent such as tetrasodium ethylenediamine tetraacetic acid or tetrasodium EDTA. Deionized water prevents the clarity and viscosity from being negatively affected due to carbopol polymers' sensitivity to hard water ions. The gel of the disclosed embodiments comprises about 37.0 percent by weight of deionized water. In an embodiment where 100 grams of said gel are produced, the gel of the disclosed embodiments comprises about 37 grams of deionized water.

Figure 4:
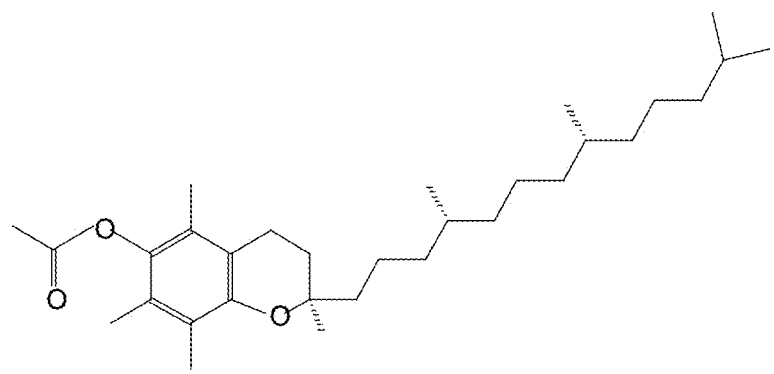
FIG. 4 is a perspective view of the molecular structure of tocopherol acetate.

"Tocopherol acetate" meaning "tocopheryl acetate," "vitamin E acetate," "DL-alpha-tocopheryl acetate," "ephynal," "syntopherol acetate," and "rovimix E 50SD" is a collective name for a group of closely related lipids that contain substitutions on the 2H-1-benzopyran-6-ol nucleus and a long hydrocarbon chain of isoprenoid units may function in the formulation as an antioxidant and skin conditioning agent, as represented by the structure 400 shown in FIG. 4.

Tocopherol acetate is a powerful antioxidant that helps to protect cell membranes, making it a great ingredient as a dry skin protector agent. The CIR Expert Panel evaluated the scientific data and concluded that tocopherol and the related ingredients were safe as used in cosmetics and personal care products. Tocopherol acetate in the formulation is required such as an antioxidant and skin conditioning agent. The gel of the disclosed embodiments comprises about 0.2 percent by weight of tocopherol acetate. In an embodiment where 100 grams of said gel are produced, the gel of the disclosed embodiments comprises about 0.2 grams of tocopherol acetate.

Figure 5:
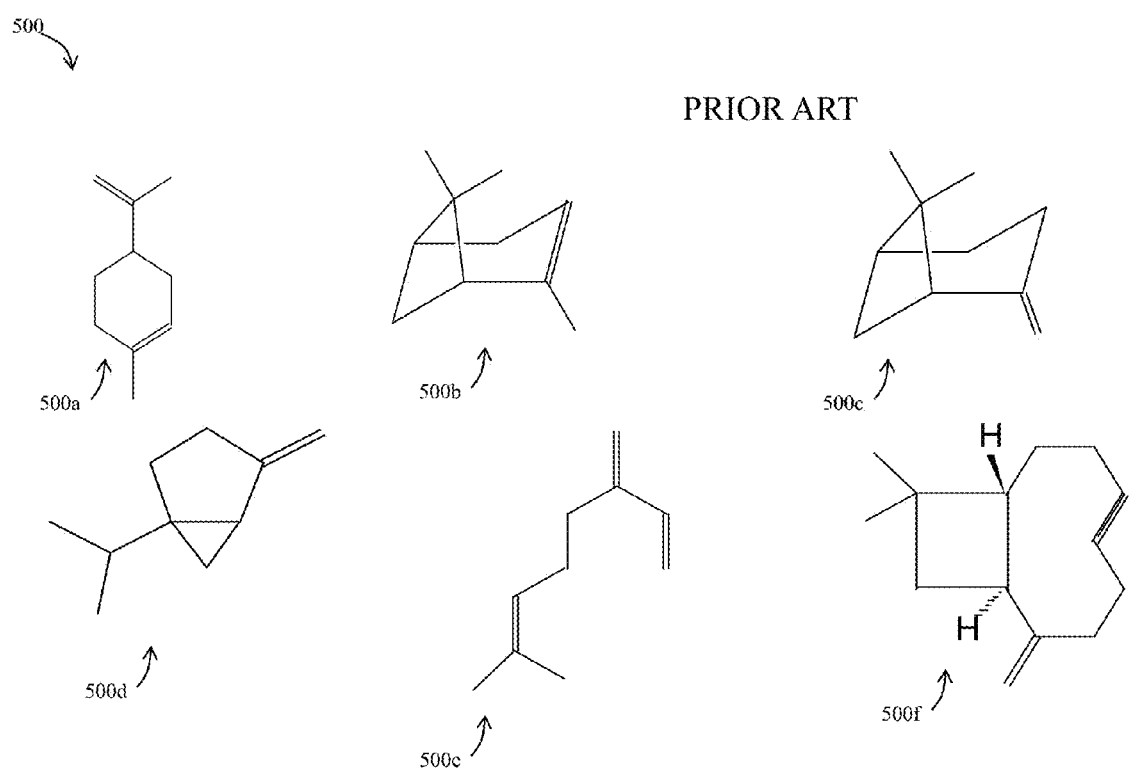
FIG. 5 is a perspective view of the molecular structure of various terpens of black pepper essential oil; 500a is the molecular structure for limonene; 500b is the molecular structure for alpha pinene; 500c is the molecular structure for beta pinene; 500d is the molecular structure for sabinene; 500e is the molecular structure for myrcene; 500f is the molecular structure for beta caryophyllene.

"Black pepper essential oil" is a clear, aromatic liquid that contains the principal components of black pepper oil. FIG. 5 is a perspective view of the molecular structures 500 of various terpens of black pepper essential oil; 500a is the molecular structure for limonene; 500b is the molecular structure for alpha pinene; 500c is the molecular structure for beta pinene; 500d is the molecular structure for sabinene; 500e is the molecular structure for myrcene; 500f is the molecular structure for beta caryophyllene. The black pepper essential oil may function in the composition as an anti-inflammatory agent. Black pepper essential oil is about 2.00 percent by weight of the total composition. In an embodiment where 100 grams of said gel are produced, the gel of the disclosed embodiments comprises about 2 grams of black pepper essential oil.

Black pepper (*P. nigrum* L.) belongs to the family Piperaceae, is the specie most known in the world and one of the renowned spices of Ayurvedic medicine with analgesic properties for muscular, joint, and nerve pain. Black pepper is used as a spice and seasoning in the processed food industry. Also, black pepper has multiple uses in perfumery, traditional medicine and even in beauty care.

Black pepper contains about 2.0-2.6% volatile oil and about 6-13% oleoresin. The black pepper essential oil contributes towards the aroma, oleoresin contributes towards the overall taste. Produced by steam distillation from the black peppercorns, the essential oil is water white to pale olive in color, with a warm, spicy (peppery) and fresh aroma. Black pepper essential oil has traditionally been used to help in the treatment of pain relief, rheumatism, chills, flu, colds, exhaustion, muscular aches, physical and emotional coldness, fevers, as a nerve tonic and to increase circulation.

The black pepper oil constituents are monoterpene hydrocarbons, sesquiterpene hydrocarbons and miscellaneous compounds. Monoterpene hydrocarbons identified in the black pepper essential oil are camphene (from 0.13 to 0.18%), δ-3-carene (from 1.03 to 2.82%), p-cymene (from 0.07 to 9.70%), limonene (from 22 to 31%); myrcene (from 2.30 to 8.40%), cis-ocimene (from 0.30 to 2.84%), α-phellandrene (from 0.2 to 2.32), β-phellandrene (from 0.20 to 0.68%), α-pinene (from 5.9 to 12.8%), β-pinene (from 10.6 to 35.5%), sabinene (from 1.94 to 17.16%), α-terpinene (from 0.39 to 1.13%), γ-terpinene (from 0.01 to 0.49%), terpinolene (from 0.08 to 0.22%), and α-thujene (from 0.73 to 1.59%). Also, there are 43 oxygenated compounds of a monoterpenoid nature have been characterized. The major sesquiterpene hydrocarbon present in pepper oil is β-Caryophyllene ranged from 22 to 28%. Other sesquiterpenes also reported in the essential oil of black pepper are α-cis-bergamotene, α-trans-bergamotene, β-bisabolene, δ- and γ-cadinenes, calamenene, α-copaene, α- and β-cubebenes, ar-curcumene, β- and δ-elemenes, β-farnesene, α-guaiene, α- and γ-humulenes, isocaryophyllene, γ-muurolene, α-santalene, α- and β-selinenes, ledene, sesquisabinene, and zingiberene.

Black pepper essential oil in the formulation of topical delivery system contains a variety of terpenes with proven medicinal activities. Limonene, α-pinene, β-pinene, sabinene, myrcene, and β-caryophyllene are the major components in black pepper essential oil. Limonene is mainly found in many citrus-peel oils, certain fruits, vegetables, and spices. Also it is used for its lemon-like flavor and odor in many food products, soaps and perfumes. The Food and Drug Administration (FDA) lists limonene as generally Recognized as Safe (GRAS) as a food additive or flavoring and a fragrance additive. The black pepper oil contains limonene in the order from 22 to 31% [60]. Limonene and pinene, the other majority compound in black pepper essential oil, have proved to present various biological activities; among them is the anti-inflammatory activity. The investigation of the inhibitory action of essential oils obtained from various plants against the production of leukotriene as a mediator of inflammation showed that (−)-menthol, (+)-limonene, α-terpinene, γ-terpinene, terpineol, β-myrcene, (±)-linalool, geraniol, citral, α-cyclocitral, (+)-α-pinene, (−)-α-pinene, and (+)-cis-verbenol was effective as an inhibitor of leukotriene production, indicating that the inhibitor can be used for a variety of inflammatory diseases, including asthma, chronic bronchitis, and allergic rhinitis, among others. On the other hand, limonene has demonstrated significant anti-inflammatory effect both in vivo and in vitro and protective effects on the epithelial barrier and decreased cytokines. The anti-inflammatory effect of limonene also involved inhibition of TNF-α (Tumor Necrosis Factor alpha) in fibroblast cultures in all animals assessed. Alpha-pinene is an acute antiseptic, while cadinene, caryophyllene, terpinene and sabinene have pronounced anti-inflammatory and antibacterial properties. Myrcene acts as a sedative, an anti-inflammatory agent and as a pain-killer for peripheral organs.

The other major component of the black pepper essential oil is the sesquiterpene β-Caryophyllene in the order of 22 to 28%. This natural product has shown having anti-inflammatory activity, but with no analgesic properties. Beta-caryophyllene (trans-caryophyllene) and Alpha-humulene inhibit the LPS-induced NF-kB activation and neutrophil migration, although only Alphahumulene had showed the ability to prevent the production of proinflammatory cytokines TNF-a and IL-1b and the in vivo up-regulation of kinin B1 receptors. Moreover, both compounds suppressed the LPS-induced neutrophil recruitment and NFkB activation, without interfering with the activation of mitogen-activated protein (MAP) kinases.

Thus, black pepper essential oil contributes through its anti-inflammatory and anesthetic properties to the formulation of the delivery system with broad spectrum anti-inflammatory. Concentrations of black pepper essential oils in the topical formulation release delivery are not health hazards.

Figure 6:
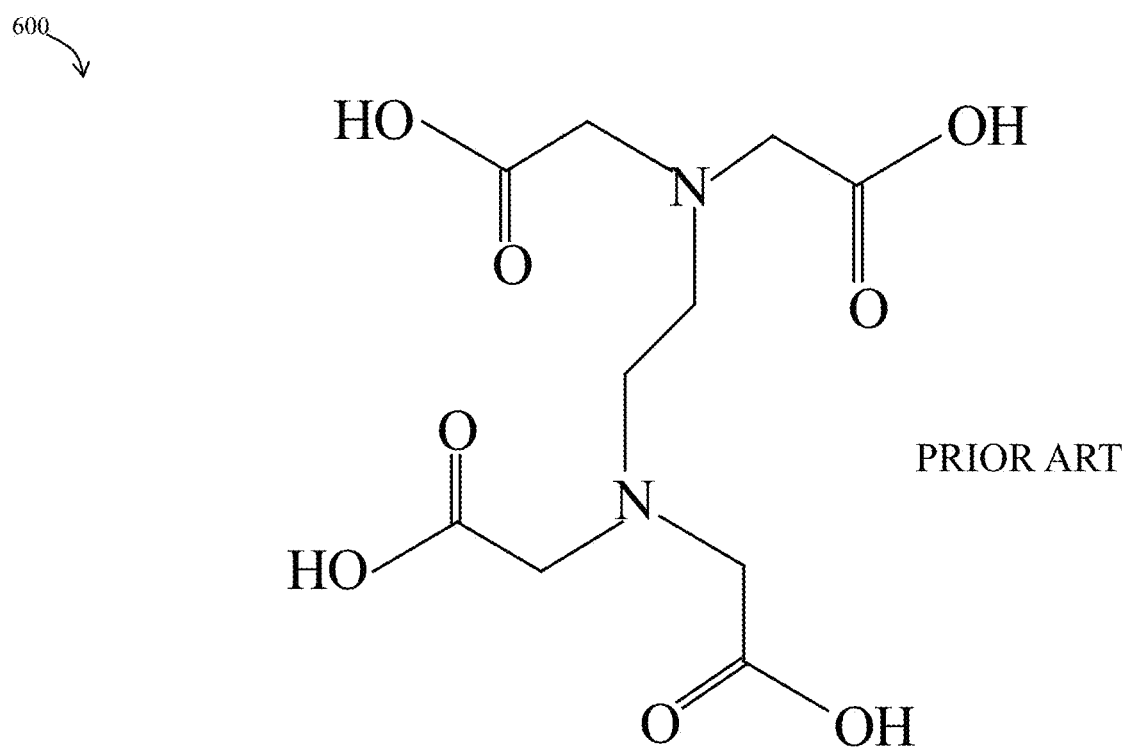
FIG. 6 is a perspective view of the molecular structure of ethylenediamine tetraacetic acid.

"Ethylenediamine tetraacetic acid" (EDTA) and its salts are crystalline powders often used in cosmetics and personal care products. EDTA binds to metal ions and helps prevent the deterioration of topical Pine bark extract and black pepper essential oil delivery system. It also contributes in maintaining gel clarity and prevent rancidity. EDTA is included in the formulation to stabilize the Carbopol® gel. If metal ions are present, they can depolymerize the carbopol with loss in viscosity, and therefore, the instability of the emulsion. EDTA is used to bind of metal ions to prevent the deterioration of formulation. It also helps to maintain clarity, protect fragrance compounds, and prevent rancidity. The formulation comprises of about 0.1 percent by weight of EDTA. EDTA is represented by the structure 600 shown in FIG. 6. In an embodiment where 100 grams of said gel are produced, the gel of the disclosed embodiments comprises about 0.1 grams of EDTA.

"Isopropyl alcohol" meaning "2-propanol," "isopropanol," "isopropyl alcohol," "propan-2-ol," "sec-propyl alcohol," "2-hydroxypropane,' and "dimethylcarbinol" is a widely used ingredient in cosmetics and personal care products and kills and prevents growth of microorganisms. Isopropyl alcohol is an alcohol that evaporates quickly. Isopropyl alcohol is a widely used ingredient in cosmetics and personal care products and can be found in products such as aftershave lotions, bath products, eye makeup, other makeup products, cleansing products, as well as nail, hair and skin care products. Isopropyl alcohol is used to dissolve other substances in cosmetics and personal care products. It is also used to decrease the thickness of liquids and to reduce the tendency of finished products to generate foam when shaken.

Isopropyl alcohol has an odor resembling ethanol and it has a slightly bitter taste. Isopropyl alcohol is volatile and produces a cooling effect upon evaporation. Rubbing alcohol consists primarily of isopropyl alcohol. Isopropyl alcohol kills and prevents the growth of microorganisms.

Figure 7:
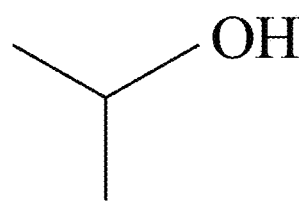
FIG. 7 is a perspective view of the molecular structure of isopropyl alcohol.

Isopropyl alcohol in the formulation is required to dissolve the black pepper essential oil and other ingredients and to provide cooling effect upon evaporation. Also it is necessary as solvent and to decrease the thickness. Furthermore it prevents the growth of microorganisms. The formulation is comprised of about 60.00 percent by weight of isopropyl alcohol. In an embodiment where 100 grams of said gel are produced, the gel of the disclosed embodiments comprises about 60 grams of isopropyl alcohol SDA. A representation of the molecular structure 700 of isopropyl alcohol is represented in FIG. 7.

Bark is the outermost layers of stems and roots of woody plants. Bark refers to all the tissues outside of the vascular cambium and is a nontechnical term that includes the following tissues: Periderm, which includes a subtissue called phelloderm; and secondary phloem. The water soluble extract of pine bark constituents are collected from the two above tissues mentioned, and belong to the large class called polyphenols. The main classes of polyphenols can be classified as phenolic acids, flavonoids, and the less common stilbenes and lignans. In turn, flavonoids can be divided into flavanols, flavones, anthocyanidins, isoflavonoids, and neoflavonoids. Flavanols (or flavan-3-ols) can exist as monomers, such as catechin, epicatechin, and its gallated forms, or as monomeric and oligomeric forms, which are referred to as procyanidins. Procyanidins were identified as the main phenolic components in pine bark. B-type procyanidins are largest procyanidins group in pine bark extracts. Procyanidins are members of the proanthocyanidin (or condensed tannins) class of flavonoids. They are oligomeric compounds, formed from stereoisomers catechin and epicatechin molecules.

Figure 8:
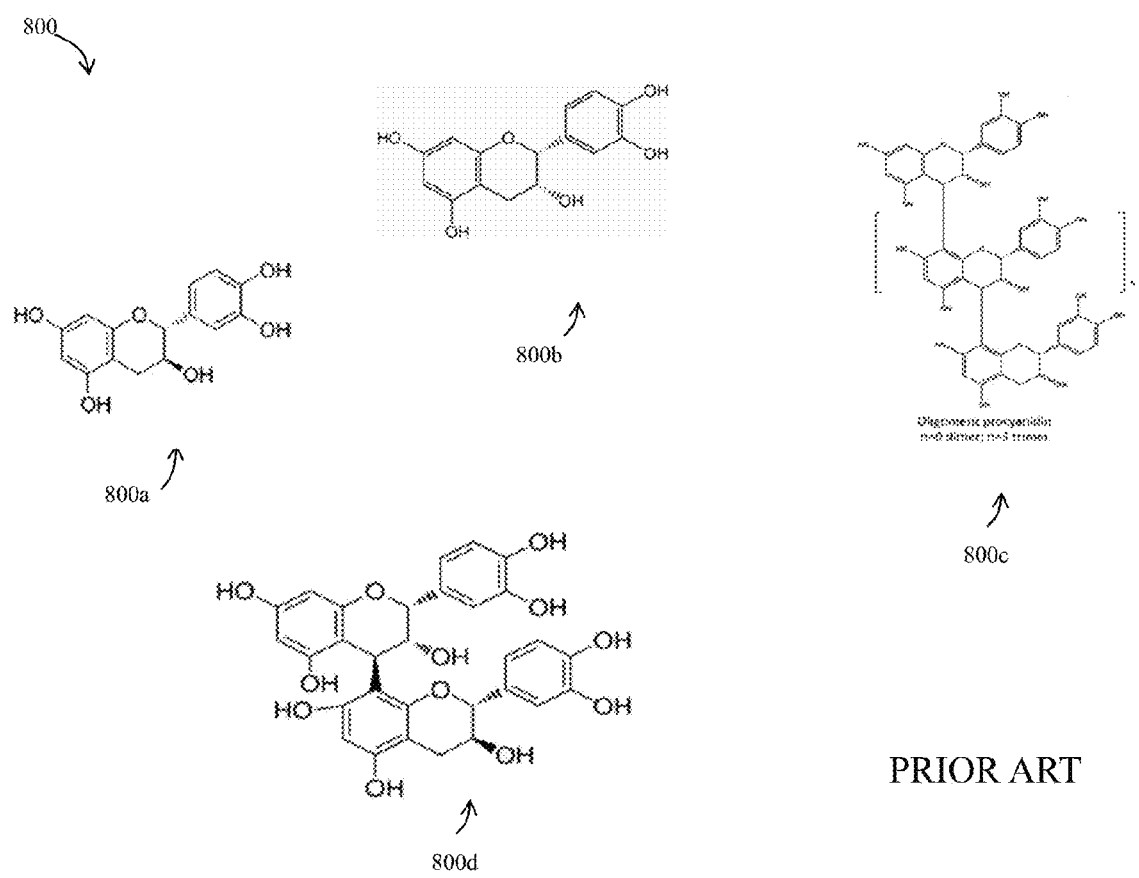
FIG. 8 is a perspective view of the molecular structure of various components of pine bar extract; catechin is represented by the structure in 800a; epicatechin is represented by the structure in 800b; a generic structure of an oligermic procyanidin is represented by the structure in 800c; a procyanidin type B, isomer 2 structure is represented by the structure in 800d.

FIG. 8 is a perspective view of the molecular structures 800 of various components of pine bar extract. Catechin is represented by the structure in 800a and Epicatechin is represented by the structure in 800b. The proanthocyanidins that consist exclusively of (epi)catechin units linked together are called procyanidins, and these are the most abundant type of proanthocyanidins in plants. Procyanidins are structurally diverse, and this diversity is based on the number of monomer units involved. Procyanidins usually occur together with monomeric (+)-catechin and (−)-epicatechin A generic structure of an oligermic procyanidin is represented by the structure in 800c A procyanidin type B, isomer 2 structure is represented by the structure in 800d. The most up to date (2014) characterization of constituents from pine bark extract is listed in the table of FIGS. 9 and 10 and peak chromatogram of FIG. 11. Again, procyanidins were identified as the larger constituent group of pine bark extract. The gel for the present formulation comprises about 0.15 percent by weight of pine bark extract. In an embodiment where 100 grams of said gel are produced, the gel of the disclosed embodiments comprises about 0.15 grams of pine bark extract.

Figure 12:
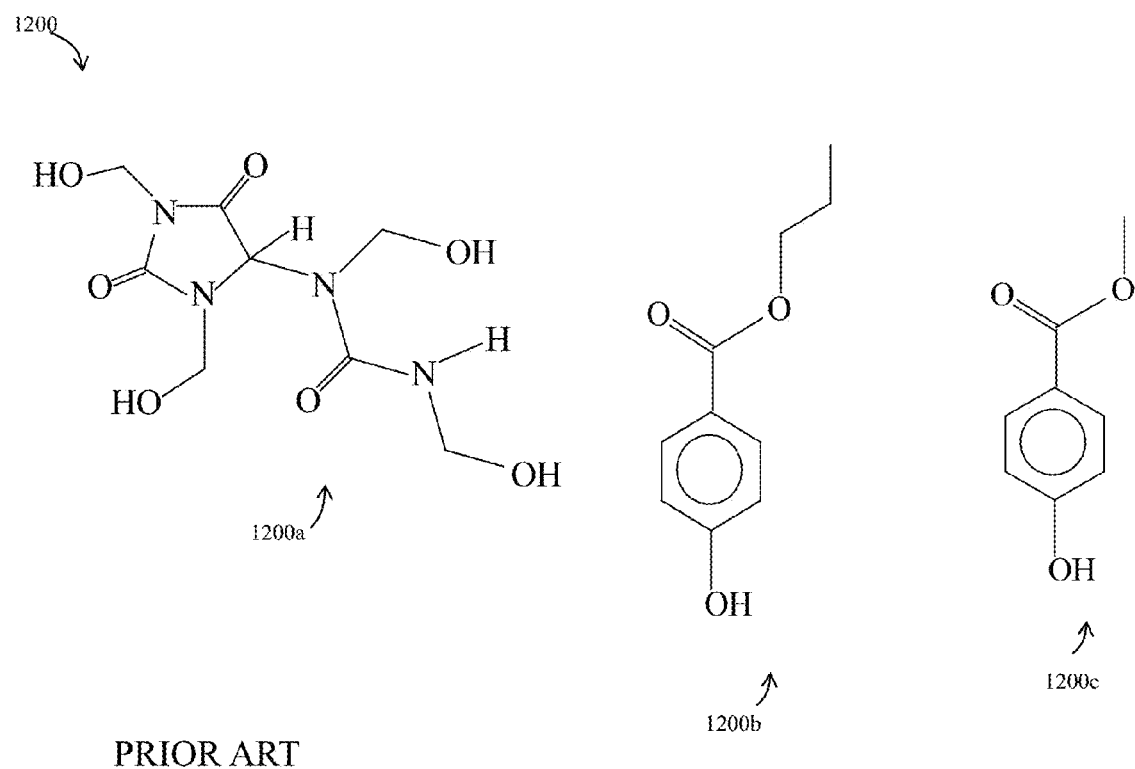
FIG. 12 is a perspective view of the components of the preservative mixture: propylparaben is represented as 700b, methylparaben is represented as 700c and diazolidinyl urea is represented as 700a; and, FIG. 13 is a flow chart illustrating the steps of preparing the disclosed pine bark extract and black pepper essential oil; and, FIG. 14 is a table of the physical properties of the disclosed pine bark extract and black pepper essential oil.

Propylparaben, methylparaben, and diazolidinyl urea in the formulation are used such as effective preservative agents. Parabens have been used for decades as preservatives in the food, drug and personal care and cosmetic industries. Diazolidinyl urea is a antimicrobial preservative used in cosmetics. They are highly effective in preventing the growth of fungi and bacteria and are used to preserve products and greatly extend their shelf life. Thus, they contribute directly to the quality of the product and, more importantly, have a proven record of safety. The formulation comprises of about 2 percent by weight of a preservative mixture solution, which itself comprises, 3 percent by weight of propylparaben 1200b and 11 percent by weight of methylparaben 1200c and 30 percent by weight of diazolinyl urea 1200a. Propylparaben may function in the formulation as a preserving agent while methaylparaben and diazolidinyl may function in the formulation as bacterial and fungi growth retardant, each of which as represented by the structures 1200 shown in FIG. 12. In an embodiment where 100 grams of said gel are produced, the gel of the disclosed embodiments comprises about 2 grams of preservative mixture solution, which itself comprises 0.06 grams of propylparaben. 0.22 grams of methylparaben and 0.6 grams of diazolinyl urea.

Figure 13:
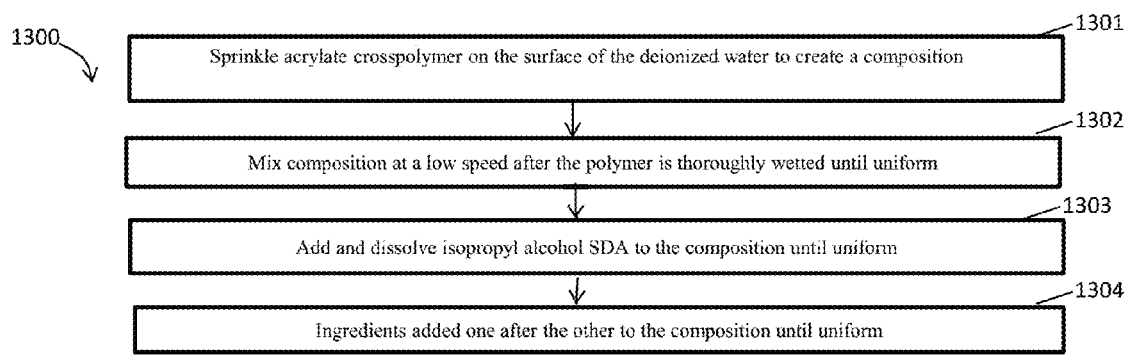

The gel for topical application with broad spectrum anti-inflammatory action is provided by a method of preparation outlined in FIG. 13. In step 1301 acrylate crosspolymer is sprinkled on a surface of deionized water. Next in step 1302, the composition is mixed at low speed until a uniform composition is formed. Next in step 1303, isopropyl alcohol, of type specially denatured alcohol (SDA), is added and dissolved in the deionized water solution and mixed until a uniform solution appearance is reached. Next in stop 1304, ingredients are added one after the other and mixed until a uniform appearance is reached. FIG. 14 is a table listing physical properties of pine bar extract and black pepper essential oil delivery system with anti-inflammatory and anti-arthritic properties.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:

1. A gel for topical application, comprising of:
   about 37.0 percent by weight of deionized water;
   about 0.3 percent by weight of acrylate crosspolymer;
   about 0.05 percent by weight of glycerin;
   about 0.2 percent by weight of tocopherol acetate;
   about 0.15 percent by weight of pine bark extract;
   about 2.0 percent by weight of black pepper essential oil;
   about 60.0 percent by weight of isopropyl alcohol SDA;
   about 0.1 percent by weight of ethylenediamine tetraacetic acid; and,
   about 2.0 percent by weight of a preservative mixture solution comprising 3 percent by weight of propylparaben, 11 percent by weight of methylparaben and 30 percent by weight of diazolinyl urea.

2. A method for preparing a gel, comprising the steps of:
   sprinkling acrylate crosspolymer on a surface of deionized water on a surface of deionized water;
   mixing acrylate crosspolymer on a surface of deionized water and the deionized water;
   dissolving isopropyl alcohol SDA in the acrylate crosspolymer and deionized water and mixing;
   adding the following ingredients: glycerin, tocopherol acetate, pine bark extract, black pepper essential oil, a preservative mixture solution comprising propylparaben, methylparaben and diazolinyl urea and mixing;
   wherein aforementioned ingredients are added to said gel in the following quantities:
   about 37.0 grams of deionized water;
   about 0.3 grams of acrylate crosspolymer;
   about 0.05 grams of glycerin;
   about 0.2 grams of tocopherol acetate;
   about 0.15 grams of pine bark extract;
   about 2.0 grams of black pepper essential oil;
   about 60.0 grams of isopropyl alcohol SDA;

about 0.1 grams of ethylenediamine tetraacetic acid; and,
about 2.0 grams of a preservative mixture solution comprising about 0.06 grams of propylparaben, 0.22 grams of methylparaben and 0.6 grams of diazolinyl urea.

3. A method for treating topical inflammation, comprising the steps of:
periodically applying said gel topically to a patient's skin, wherein the gel comprises:
about 37.0 percent by weight of deionized water;
about 0.3 percent by weight of acrylate crosspolymer;
about 0.05 percent by weight of glycerin;
about 0.2 percent by weight of tocopherol acetate;
about 0.15 percent by weight of pine bark extract;
about 2.0 percent by weight of black pepper essential oil;
about 60.0 percent by weight of isopropyl alcohol SDA;
about 0.1 percent by weight of ethylenediamine tetraacetic acid; and,
about 2.0 percent by weight of a preservative mixture solution comprising 3 percent by weight of propylparaben, 11 percent by weight of methylparaben and 30 percent by weight of diazolinyl urea.

* * * * *